United States Patent [19]

Ashmead

[11] 4,172,072

[45] Oct. 23, 1979

[54] BUFFERED ENZYMATICALLY PRODUCED METAL PROTEINATES

[76] Inventor: Harvey H. Ashmead, P.O. Box 750, Clearfield, Utah 84015

[21] Appl. No.: 843,971

[22] Filed: Oct. 20, 1977

[51] Int. Cl.$^2$ .................. C07G 7/04; A61K 37/00; A61K 31/66
[52] U.S. Cl. .................. 260/115; 435/272; 260/112.5 R; 260/113; 260/429 J; 424/177; 562/553; 562/567
[58] Field of Search .................. 195/29; 260/113, 115, 260/112.5 R, 429 J; 562/553, 567

[56] References Cited

U.S. PATENT DOCUMENTS

| 3,344,130 | 9/1967 | Mortenson | 260/115 |
|---|---|---|---|
| 3,396,104 | 8/1968 | Miller | 210/54 |
| 3,775,132 | 11/1973 | Richards | 426/364 |
| 3,857,966 | 12/1974 | Feldman et al. | 426/7 |
| 4,020,158 | 4/1977 | Ashmead et al. | 424/177 |

*Primary Examiner*—Walter C. Danison
*Attorney, Agent, or Firm*—Criddle, Thorpe & Western

[57] ABSTRACT

Protein sources are subjected to hydrolysis by the action of specific proteases under neutral conditions and are then reacted with water soluble bivalent metal salts in an aqueous alkaline media to form metal proteinates which are then buffered thereby forming biologically acceptable metal proteinates which are protected from adverse acid or alkaline destruction.

7 Claims, No Drawings

BUFFERED ENZYMATICALLY PRODUCED METAL PROTEINATES

BACKGROUND OF THE INVENTION

This invention relates to the preparation of biologically acceptable bivalent metal coordination complexes. More particularly this invention relates to the hydrolysis of proteinaceous materials under neutral conditions and to the preparation of metal coordination complexes utilizing the protein hydrolysates as ligands.

Metal coordination complexes and more particularly metal proteinates are known in the art to increase the level of bivalent metals in the tissues of both plant and animal organisms.

U.S. Pat. No. 3,873,296 teaches the use of metal proteinates in increasing the levels of essential bivalent metals in plant tissues. A method of increasing bivalent metals in animal tissues utilizing metal proteinates is claimed in copending application Ser. No. 658,243, filed Feb. 11, 1976 and now U.S. Pat. No. 4,020,158.

Metal proteinates are defined as coordination complexes of two or more protein hydrolysate ligands with a metal ion having a valence or oxidation state of at least +2.

There are many products identified in the literature as being reaction products of proteins or protein hydrolysates with metals which are salts or complexes of sorts but most are not metal proteinates.

For example, U.S. Pat. No. 1,824,018 teaches combinations of iron and copper compounds for the treatment of anemia. As related to the present invention, the example showing the combination of copper caseinate and iron peptonate is perhaps most pertinent. Copper caseinate is a combination of copper with casein which has not been hydrolyzed and which may be defined as an insoluble protein salt. This product may be described as the interaction of a metallic copper with an intact protein, but does not produce a metal proteinate or coordination complex as hereinafter described. Likewise, this patent discloses an iron peptonate. Iron peptonate is described in the National Formulary V as a compound of iron oxide and peptone rendered soluble by the presence of sodium citrate. Again, this is not a metal proteinate or coordination complex as will be described.

U.S. Pat. No. 505,985 describes an iron albumen preparation which is a combination of an unhydrolyzed protein which has been heat coagulated. The iron present attaches itself to the surface of the protein molecule and a precipitate is formed. According to the patent this product is readily soluble in a weakly alkaline solution. It cannot therefore be considered to be a metal coordination complex formed from a protein hydrolysate for such a product would be insoluble in basic solution.

U.S. Pat. No. 2,481,413 teaches the preparation of metal caseinates which again are salts or compounds of a protein molecule with metal ions attached thereto, but are not metal coordination complexes.

A more recently issued patent, U.S. Pat. No. 2,960,406 teaches soluble trace metals which are allegedly coordination complexes, preferably using EDTA as a complexing agent. According to that patent, when any of the described metal salts are introduced into water, metal coordination complexes will form in the water solution. While EDTA and its salts are strong complexing agents protein hydrolysates such as naturally occurring amine acids, peptides and polypeptides will not form a coordination complex merely by their combination with a soluble metal salt in water. Therefore, while U.S. Pat. No. 2,960,406 may teach coordination complexes with EDTA and its derivatives, there are insufficient data in the patent to teach the preparation of metal proteinates. The mere combination of a metal salt and a naturally occurring amino acids or protein hydrolysate in an aqueous solution is insufficient for reasons later hereinafter described.

Additionally, U.S. Pat. No. 3,463,858 teaches a process of making a feed additive by slurrying a mixture containing an amino acid source and a water soluble zinc salt, heating, acidifying and drying the slurry. Since this patent teaches that the optimum pH for combining zinc with amino acids is about 3.5, this is inimical to coordination complex formation.

Essential metals such as iron, zinc, copper, magnesium, manganese, calcium, cobalt, molybdenium and chromium are capable of existing in bivalent form. By "bivalent" is meant the metals may assume an ionic or oxidation state of at least +2 or higher.

Since, in general, these metals, as inorganic or organic salts, including those described in the above prior art, are absorbed into the body with difficulty, it is desirable to formulate these metals as proteinates so that they can be effectively assimilated into the body. Salts ionize in the gastric juices of the stomach and enter the small intestine, where most absorption takes place. The intestinal walls are lined with electrical charges which have a strong tendency to repel the positive metal cations while allowing the aninons to pass through. The essential metals are thus discharged through the bowel often causing diarrhea. The anions passing through the intestinal wall often are excreted via the urine and may act as diuretics.

It would therefore be beneficial to prepare a formulation of an essential bivalent metal in a form whereby the effects of the electrical charges of the intestinal lining of the metal were minimized and whereby the metal could readily pass through the acid stomach juices and be made available to the body in a ready assimilable form.

In the past it has been known to utilize certain protein hydrolysates as complexing agents or ligands to increase the assimilation of metals into biological tissues. It has been found however that certain protein hydrolysates are poor ligands due to their size and stereo chemistry. Long chain polypeptides when used as ligands do not form as strong a bond with a metal ion in coordination complex formation as do amino acids, dipeptides and tripeptides. It is therefore axiomatic that coordination complexes formed from metal ions and long chain polypeptides are more easily destroyed in the acidic gastric juices of the stomach.

Protein hydrolysates is a term generally used for any form of hydrolyzed protein ranging from the above mentioned long chain polypeptides down to the basic protein building blocks, i.e. amino acids. These hydrolysates are commonly formed utilizing acidic or basic hydrolysis or a combination of both. Since many different amino acids are essential to the body there is a distinct disadvantage to the utilization of either form of hydrolysis. Acidic hydrolysis destroys the amino acids tryptophan, serine and theonine. On the other hand, basic hydrolysis racemizes the amino acids into their D. and L. forms and destroys arginine, threonine, serine, and cystine. Naturally occurring amino acids belong only to the L-series. Moreover acidic and basic hydrolytic processes require neutralization and this results in the formation of inorganic salts which often remain with and form a material part of the hydrolyzed product.

U.S. Pat. No. 3,396,104 teaches a process for the indiscriminate preparation of metal proteinates utilizing a protein source with saline water and hydrolyzing the protein by a base-acid process to form a proteinate of sorts. The product is not well defined and may vary greatly in mineral content as well as ligand.

An improvement to the above mentioned process is disclosed in U.S. Pat. No. 3,775,132 wherein the protein is subjected to a base-acid-base hydrolysis step and then admixed with a metal salt in alkaline media to form a proteinate.

An enzymatic form of hydrolysis is taught in U.S. Pat. No. 3,857,966 wherein a protein hydrolysate is formed in a two step process wherein a protein source is heat treated under basic conditions and reacted with an alkaline microbial protease and then reacted in a second step at a neutral pH with both a plant enzyme and a neutral microbial protease.

All of the above process are multistep methods requiring at least two different hydrolysis phases.

A milder form of hydrolysis is taught in U.S. Pat. No. 3,969,540 wherein a protein source is enzymatically hydrolyzed under essentially neutral conditions to a polypeptide stage with the hydrolysis being sufficiently mild that no single amino acids are formed. The hydrolysis is not complete and thus the metal proteinate subsequently formed under alkaline conditions contains relatively large amounts of unhydrolyzed or partially hydrolyzed protein such as muscle, heart, liver and the like.

OBJECTS AND BRIEF DESCRIPTION OF THE INVENTION

It is an object of the present invention to substantially completely enzymatically hydrolyze proteins under neutral pH conditions, to prepare metal proteinates therefrom in an alkaline aqueous media and to buffer the metal proteinates at an alkaline pH as that they will be protected from acidic and extreme alkaline conditions.

It is also an object of this invention to enzymatically hydrolyze proteins to form a majority of tripeptides, dipeptides and amino acids under neutral reaction conditions and then forther react said hydrolysates with a biologically essential bivalent metal to form metal proteinates at a pH between about 7.5 and 10.

A still forther object of the present invention is to enzymatically hydrolyze a source high in protein under neutral conditions; to form a buffered metal proteinate from the hydrolyzed protein and to buffer the metal proteinate thus formed at an alkaline pH between 7.5 and 10.

These and other objects may be attained by enzymatically digesting or hydrolyzing a protein source such as collagen, gelatin, albumin or casein with a protease. There are many different types of proteases i.e., bacterial, fungal, plant, etc. Particularly efficacious are the plant proteases such as papain, bromelin or bromelain, and ficin.

Once hydrolysis is essentially complete the metal salts may be dissolved in the solution and the solution is raised to an alkaline pH to form a metal proteinate which is then buffered with an alkaline buffer such as potassium or sodium phosphate or carbonate salts or mixes thereof. Examples of salts include $KHPO_4$, $KH_2PO_4$, $Na_2CO_3$ and $NaHCO_3$. The buffering maintains the pH between about 7.5 and 10.

DETAILED DESCRIPTION OF THE INVENTION

It has now been found that essential bivalent metals are more effectively administered to animals in the form of a buffered coordination complex formed from tripeptides, dipeptides and naturally occurring amino acids wherein the ligand to metal mole ratio is between two and sixteen. Preferable the mole ratio of ligand to metal will be between two and eight. Especially preferred are ratios between two and four. Each ligand will have a molecular weight varying between about 75 and 750.

As previously mentioned the ligands will advantageously be formed by the enzymatic hydrolysis of protein sources such as collagen, isolated soya, yeast, casein, albumin, gelatin and the like. Enzymatic hydrolysis utilizing enzymes, such as trypsin, pepsin, and preferably, plant proteases is not detrimental to the formation of L-amino acids. Ligands prepared by enzymatic hydrolysis do not contain inorganic salts that ligands from basic or acidic hydrolysis may have. The term naturally occurring amino acids also includes synthetically produced amino acids having the same stereo configuration as those which occur in nature. Proteins yield over twenty amino acids including glycine, alanine, valine, leucine, isoleucine, phenylalanine, tryosine, tryptophan, serine, threonine, aspartic acid, asparagine, glutamic acid, glutamine, lysine, arginine, histidine, cystine, cysteine, methionine, proline and hydroxy proline. A dipeptide is a combination of two amino acids and one peptide bond. A tripeptide is a combination of three amino acids with two peptide bonds. The ligands bonded to a metal ion can be the same or different.

When making the chelates the shorter the chain length of the ligand the easier it is to form coordination complexes and the stronger the bonds will be. As used herein the term coordination complexes and proteinate may be used interchangeably unless a non-protein derived ligand is referred to.

It is beneficial to first hydrolyze a protein source well so that the major portion of the hydrolysates will be amino acids, dipeptides and tripeptides. Thus after coordination complexing is accomplished through pH adjustments, the subsequent or buffered formation of the metal proteinate can form a product that is protected against pH shift and can be actively transported through the body tissues. Large protein entities such as metal salts of gelatinates, caseinates or albuminates must be broken down or hydrolyzed before transport can take place. It is believed that unhydrolyzed protein salts, in general, are unabsorbed from the intestinal walls. Therefore, in the present invention the protein molecules are hydrolyzed to a tripeptide, dipeptide or amino acid stage prior to mixing with the metal salt. In order to form a metal proteinate the proper amounts of constituents myst be present at the right conditions. The mineral to be used must be in soluble form and the tripeptides, dipeptides or amino acids must be free from interfering protons, i.e., non-intact, in the complexing process so that chemical bonds can be formed between the proteinate ligand and the metal involved. Since coordination complexes, by definition, are molecular structures in which a heterocyclic ring can be formed by the unshared electrons of neighboring atoms, it is essential that before a protein hydrolysate can complex with a metal ion to form coordinate bonds, that the protons in the complexing agent, i.e., the amino acid, dipeptide or tripeptide be removed. Again, by definition, a complexing agent is considered to be an organic compound in which the atoms contain donor electrons which form more than one coordinate bonds with metal ions in solution. Thus it is essential that the complexing process takes place in alkaline solution. Once the mineral salt is completely soluble and the amino acids or peptides are sufficiently soluble, the pH must be adjusted to a point that is sufficiently basic to remove interfering protons from both the amine groups and the carboxyl groups of the ligands. While a pH of 7.5 may be sufficient a pH in the range of 8-10 is preferred. This allows the heterocyclic rings to form bonds between the metal and lone pairs of electrons left behind on the amine groups. The subsequent addition of a buffer serves to keep the pH constant to assure that the proteinate has stability in acid or alkali which could shift the pH of an unprotected proteinate. Thus, the mere mixing of intact amino acids or intact peptides with water in the presence of a metal salt will not result in a proteinate because the protons on the carboxyl and amine groups interfere with proteinate formation. When combining protonated or intact peptides or amino acids with a soluble metal salt either no reaction takes place or a salt may be formed from the metal with the peptide or amino acid, which salt may be soluble or may precipitate. The metal proteinates or coordination complexes are heterocyclic complexes and are vastly different from metal salts of peptides or amino acids. The metal proteinates are more readily assimilated making the metal more readily available to the body tissue in buffered form.

The coordination number, which is quite different from the valence tells how many coordinate covalent linkages a metal may have. Using iron as an example, the number may vary from two to eight although other values are also known. The ferrous ion, may have four or more waters of hydration. Since most metals have coordination numbers of two to eight their ions become encased within hydration shells made up of waters of hydration wherein each electronegative oxygen atom of each water molecule is attracted to the positively charged metal ion.

Every bond between the metal, in this case iron, and oxygen atoms consists of two electrons. The water molecules are said to be coordinated to the metal because each oxygen atom contributes both electrons that make up the coordinate covalent or simply covalent bonds.

A complex is formed when a substance other than water forms a coordinate or covalent bond. Not all complexes are coordination complexes. Oxygen and nitrogen are electronegative elements that contribute electron pairs to form covalent bonds. Amino acid and peptide ligands contain both of these electronegative elements. A ligand may refer to the part of a molecule which contains these negatively charged elements and is the site where complex formation occurs. The term "ligand" is also used to designate the metal binding molecules themselves. When a metal proteinate has two or more ligands it may be referred to as a bi-, tri-, quadri-, quinque-, or sexadentate proteinate, etc.

To form a metal proteinate the coordinated water molecules will be replaced by the ligand.

Coordination complexes differ from salts and other complexes due to their closed ring structure in which the metals are tightly held. Generally five membered rings are most stable. It is to be remembered that while covelant bonds are most stable and are preferred some ionic bonding may be formed in each coordination complex. The transition metals bends to form more stable covalent bonds whereas alkaline earth metals are more likely to contain some ionic bonds.

Stability constants may be determined by polarography wherein it is shown the coordination complexes are of the magnitude of $10^3$ to $10^{13}$ times more stable than the corresponding salts or complexes.

Using glycine, the simplist amino acid, as a model and iron as the metal ion containing four waters of hydration the reaction would be as follows:

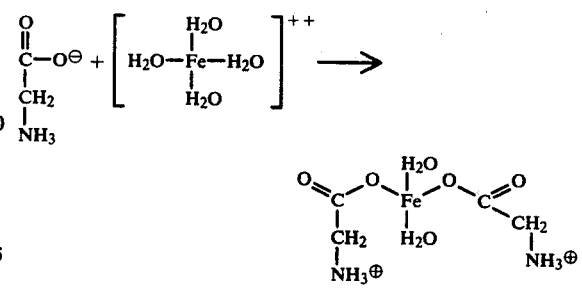

Thus, a complex is formed which may or may not be soluble in the aqueous reaction media. Upon the addition of more base such as NaOH the product becomes

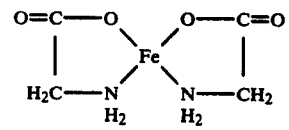

This represents a true metal proteinate wherein all of the protons on the ligand have been removed and thus heterocyclic rings have been formed. Note that each ring has five members which are found to be most stable. From the above it is imperative that the ligand protons be removed and full complexing be carried out under basic reaction conditions prior to buffering.

Buffered metal proteinates in general are relatively insoluble in basic solutions but depending upon the concentration, metal proteinates at low concentrations are soluble or partially soluble in slightly acidic to alkaline solutions.

When administering metal proteinates orally to warm blooded animals a portion of the product may be destroyed by the acidic media of the stomach thus depriving the animal from the full benefit of the dosage adminisitered. It has been shown, however, that by buffering, a major proportion of the metal proteinates are passed intact into the intestine for absorption.

The metal proteinate can be stabilized and thus pass more readily through the stomach when buffered to a constant pH between about 7.5 and 10. The buffer system may change according to the metal proteinate being administered, and one or more metal proteinates may be administered at one time.

The choice of buffer system will depend upon the pH desired. Amino acids alone will react with bases such as sodium hydroxide to form buffered systems. Typical buffer solutions include phosphate, carbonate and bicarbonate anions or combinations thereof. Examples of typical buffering systems in the pH range of 7 to 10 are as follows:

| pH | |
|---|---|
| 7 | 9.1g. KH$_2$PO$_4$ + 19.7g. Na$_2$HPO$_4$ per liter. |
| 8 | 50 ml. M/5 KH$_2$PO$_4$ + 22.4 ml. M/5 NaOH diluted to 200 ml. |
| 9 | 50 ml. M/5 KH$_2$PO$_4$ + 46.1 ml. M/5 NaOH diluted to 200 ml. |
| 10 | 6.5g. NaHCO$_3$ + 13.2g. Na$_2$CO$_3$ per liter. |

The present invention encompasses any combination of organic or inorganic substituents which will buffer or maintain a system at a pH range of 7.5 to 10. There are numerous other buffering systems readily available to one with ordinary skill in the art and mere enumeration would be redundant. What is important to the invention is that a buffering system be selected which will not only help form and stabilize a metal proteinate but will also be non-toxic and assist in the assimilation of the metal proteinate into the body.

A distinct advantage of the present invention, as will be illustrated in the examples, is that the hydrolysate and coordination complex formation can take place in a single vessel without changing solutions, filtering ingredients or other costly and time consuming operations. When hydrolysis is complete the solution is merely brought to a boil to stop the enzymatic action and sufficient metal salt and bases are added to bring about proteinate formation prior to buffering.

The products of the invention are intended for use in plants and all species of the animal kingdon including man.

The dosage to be administered will depend upon the type of formulation, the animal species, weight, age, sex and the metal proteinate or mixture of metal proteinates being administered. It may first be desirable to determine the metal deficiencies in an animal by assaying hair, nails, blood, urine, skin or saliva from the animal and comparing the results with a standard representing a normal healthy animal of the same species. A corrective buffered formulation can then be made up. On the other hand it may be desirable to administer the RDA (recommended daily allowance) of each metal in one or more dosages. For example, the RDA for an average adult is, Iron 18 mg.; Zinc 15 mg.; Copper 2 mg.; Magnesium 400 mg. and Calcium 1000 mg. or 1 gram. There have been no RDA's set for other minerals which have been considered essential to the proper functioning of the body.

The buffering metal proteinates prepared by the above method can be given in various ways as long as a biologically effective amount is administered. When administered orally the metal proteinates can be admixed with a suitable carrier and given in the form of tablets, pills, capsules, emulsions, syrups or admixed with, sprinkled over or poured over the animals food.

When given to human subjects the metal proteinates may be administered as a tablet, pill, syrup, capsule or the like or may be admixed with or placed on the surface of foods such as stews, meats, bakery products, candies, deep fried foods or placed in seasonings or spices.

To show the preparation of buffered metal proteinates as herein described and their ability to raise the level of metals in biological tissues the following examples are given. It is to be noted however that the examples are not intended to be self limiting but are for purposes of illustration only.

EXAMPLE 1

A mixture of 200 lbs. of collagen and 1000 lbs. of water was mixed in a jacketed tank and stirred. Two lbs. of papain (a plant protease) was added along with 200 gms. of sodium benzoate as a preservative. The solution had a substantially neutral pH. The mixture was covered and constantly stirred at a temperature of 71° C. for 20 hours. A protein hydrolysate consisting primarily of tripeptides, dipeptides and amino acids was formed. The digested mixture was brought to a boil to kill the enzymatic action. Into this mixture was dissolved 135 lbs. of FeSO$_4$.7H$_2$O. The molar ratio of protein hydrolysate ligand to iron was at least 2:1. The solution was made alkaline by the addition of 40 lbs. of sodium hydroxide to effect complex formation and raise the pH to 8. A precipitate immediately formed which, upon analysis, was found to be an iron proteinate. The iron proteinate was buffered at a pH of 8 using a mixture of sodium hydroxide and sodium bicarbonate as the buffer. The buffered proteinate was found to be about $10^5$ times more stable than the unbuffered compound.

EXAMPLE 2

Into a container was placed 85 lbs of water, one-half lb. of the plant enzyme ficin, 45 grams of sodium benzoate and 45 grams of sodium propionate as preservatives. The combined mixture was stirred well. There was then added 45 lbs. of collagen in comminuted form. The mixture was constantly stirred at a temperature of 145° F. for eight hours. At the end of this period of time hydrolysis was substantially complete and the majority of collagen had been hydrolyzed to tripeptides, dipeptides and amino acids. The mixture was stirred and boiled to kill the enzyme and was allowed to cool. Since collagen is deficient in sulfur containing amino acids there was then added 2 lbs. of 1-methionine. To this mixture, under neutral conditions, was added 50 lbs. of ferrous sulfate (FeSO$_4$.7H$_2$O). Sufficient sodium hydroxide was added to bring the pH to about 9.5 thereby forming a precipitate which was found to be an iron proteinate. The ligand to metal ratio was greater than 2:1. The proteinate was buffered to a pH of 9 using a combination containing 2 parts by weight of sodium hydroxide and 1 part by weight of sodium carbonate. There was then added to the buffered proteinate solution 44 lbs. of wheat middlings onto which the buffered iron proteinate was absorbed. The combined wheat middling, buffered iron proteinate mixture was separated from the solution and allowed to dry at 145° F. for 48 hours. Upon analysis the mixture was found to contain about 8.25% iron in the form of a buffered iron proteinate.

EXAMPLE 3

A formulation suitable for feeding to swine was prepared by mixing together 11 lbs. of water, 23 grams of sodium benzoate, 23 grams of sodium propionate and 0.18 lbs. (82 grams) of bromelain, a plant enzyme. The mixture was stirred well and there was then added 18 lbs of collagen. Enzymatic hydrolysis was allowed to continue overnight thus breaking the collagen into primarily amino acids, dipeptides and tripeptides to which was then added one lb. of 1-methionine. The mixture was brought to a boil to kill the enzymatic action. Soluble metal salts were then added to the solution in the form of 14 lbs. of ferrous sulfate ($FeSO_4 \cdot 7H_2O$); 3.42 lb. of zinc chloride ($ZnCl_2$) and 0.63 lbs. of copper sulfate ($CuSO_4 \cdot 7H_2O$). The metal salts were dissolved under neutral conditions into the soluble protein hydrolysates. Sufficient sodium hydroxide was added to raise the pH to about 8.5 thereby precipitating a mixture which upon analysis was found to consist of iron, zinc and copper proteinates. The same buffer as used in Example 2 was then added to buffer the proteinates to a pH of about 9. The buffered proteinates were then adsorbed onto 14 lbs. of wheat middlings and allowed to dry at a temperature of 145° F. The dried product analyzed about 5.49% iron, 3.64% zinc and 0.36% copper in buffered proteinate form.

EXAMPLE 4

The hair of twelve swine was analyzed for iron, zinc and copper content and six swine were used as a control group and the other six swine were fed the composition formed in Example 3 at a rate of 5 lbs. of metal proteinates per ton of feed. Sixty days after treatment was begun the hair was again analyzed. The hair of the treated swine contained 28% more iron, 21% more zinc and 19% more copper on the average than did the controls.

EXAMPLE 5

The blood of five human volunteers was analyzed for hemoglobin content. After blood analysis each volunteer was given 18 mg. of iron daily, i.e. the Recommended Daily Allowance, in the form of a buffered iron proteinate as formed in Example 1. After 45 days of treatment the blood was again analyzed and was found to contain 14% more hemoglobin than at the beginning of treatment.

EXAMPLE 6

Twelve tomato plants were allowed to grow to about the three leaf stage. Six plants were given a mixture of iron and magnesium sulfates and six were treated by administering the same amount of iron and magnesium in the form of iron and magnesium proteinates which had been buffered to a pH of about 7.8. All twelve tomato plants received the same amount of water and light. At the end of three weeks the treated plants were about three inches taller than comparable plants treated with inorganic iron and magnesium salts.

I claim:

1. A method of preparing buffered metal proteinates which comprises the steps of,
    (a) hydrolyzing a protein source in the presence of an enzyme under substantially neutral conditions to form a soluble aqueous mixture consisting primarily of tripeptides, dipeptides and naturally occurring amino acids,
    (b) dissolving into the mixture under neutral conditions at least one bivalent metal salt wherein the molar ratio of tripeptides, dipeptides and amino acids to metal ions is at least 2:1,
    (c) adding sufficient base to the aqueous mixture to raise the pH to between about 7.5 and 10 thereby forming one or more metal proteinates, and
    (d) buffering said metal proteinates with an alkaline buffer to a pH of between about 7.5 and 10.

2. A method according to claim 1 wherein the metal is selected from the group consisting of iron, zinc, manganese, cobalt and calcium.

3. A method according to claim 2 wherein the enzyme is a plant enzyme.

4. A method according to claim 3 wherein the hydrolysis is carried out at an elevated temperature.

5. A method according to claim 4 wherein the buffer contains a phosphate or carbonate salt of potassium or sodium.

6. A buffered metal proteinate prepared according to the process of claim 5.

7. A buffered metal proteinate according to claim 6 wherein the metal is iron.

* * * * *